(12) United States Patent
Arnold et al.

(10) Patent No.: US 10,590,453 B2
(45) Date of Patent: Mar. 17, 2020

(54) METHODS FOR AMPLIFICATION OF NUCLEIC ACIDS UTILIZING A CIRCULARIZED TEMPLATE PREPARED FROM A TARGET NUCLEIC ACID

(71) Applicants: Lyle J. Arnold, Poway, CA (US); Norman C. Nelson, San Diego, CA (US)

(72) Inventors: Lyle J. Arnold, Poway, CA (US); Norman C. Nelson, San Diego, CA (US)

(73) Assignee: AEGEA BIOTECHNOLOGIES, INC., Poway, CA (US)

( * ) Notice: Subject to any disclaimer, the term of this patent is extended or adjusted under 35 U.S.C. 154(b) by 32 days.

(21) Appl. No.: 15/998,679

(22) Filed: Aug. 16, 2018

(65) Prior Publication Data
US 2019/0112625 A1 Apr. 18, 2019
US 2020/0002740 A9 Jan. 2, 2020

Related U.S. Application Data

(62) Division of application No. 14/773,363, filed as application No. PCT/US2014/029829 on Mar. 14, 2014, now Pat. No. 10,081,825.

(60) Provisional application No. 61/789,521, filed on Mar. 15, 2013.

(51) Int. Cl.
C12P 19/34 (2006.01)
C12Q 1/6844 (2018.01)

(52) U.S. Cl.
CPC ............ *C12P 19/34* (2013.01); *C12Q 1/6844* (2013.01)

(58) Field of Classification Search
None
See application file for complete search history.

(56) References Cited

U.S. PATENT DOCUMENTS

2006/0166245 A1* 7/2006 Potter et al.

* cited by examiner

*Primary Examiner* — Young J Kim
(74) *Attorney, Agent, or Firm* — David B. Waller

(57) ABSTRACT

The present invention provides methods of amplifying a target nucleic acid utilizing a circularized template. Circularization may be achieved utilizing a bridging oligonucleotide or an inverter primer. The bridging oligonucleotide or inverted primer is extended forming a concatemeric amplicon that can then be used as a template to provide exponential amplification of the target nucleic acid.

3 Claims, 7 Drawing Sheets

METHODS FOR AMPLIFICATION OF NUCLEIC ACIDS UTILIZING A CIRCULARIZED TEMPLATE PREPARED FROM A TARGET NUCLEIC ACID

CROSS-REFERENCE TO RELATED APPLICATIONS

This application is a divisional application of patent application Ser. No. 14/773,363 filed Sep. 7, 2015, which is a non-provisional application of provisional patent application Ser. No. 61/789,521 filed Mar. 15, 2013 and claims the benefit of the filing date of PCT/US2014/029829 filed 14 Mar. 2014 under 35 U.S.C. § 371 from which the PCT application claims priority.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION

(1) Field of the Invention

The present invention relates to methods of amplifying nucleic acids. Specifically, exponentially increasing amplification yields utilizing a circularized template prepared from a target nucleic acid.

(2) Description of Related Art

There are a variety of nucleic acid amplification methods currently used in the life sciences industry and some of these utilize a rolling circle amplification technique. A few of these techniques amplify target nucleic acids in a linear fashion and as such lack the sensitivity for many desired applications. Some of these methods amplify target nucleic acids in an exponential fashion, but can be time consuming, tedious, difficult to automate and often lack the required sensitivity, precision, reproducibility and multiplexing capability. A method that is simple to perform, rapid, sensitive, specific, precise, accurate and reproducible is needed. It would also be beneficial if such a method was able to detect multiple target nucleic acids in a single assay (i.e., multiplexing, including high level multiplexing), perform these reactions under isothermal conditions and conduct these methods utilizing less complex equipment. These improvements would positively affect current sequencing procedures, development of in vitro diagnostics as well as a wide variety of other applications by reducing assay costs, decreasing the time for obtaining results and providing ease of use. The present invention describes methods that resolve these disadvantages and provide the benefits discussed.

BRIEF SUMMARY OF THE INVENTION

The present invention provides methods to perform target specific exponential rolling circle amplification comprising a variety of embodiments to re-prime amplicons that support multiple cycles of amplification.

One aspect of the present invention is a method of amplifying a nucleic acid utilizing a circularized nucleic acid template. The method comprises a number of steps beginning with first and second primers and a bridging oligonucleotide being mixed with a target nucleic acid. The first primer comprises a sequence complementary to a first portion of the target nucleic acid. The second primer comprises a sequence identical to a second portion of the target nucleic acid and a first cassette at its 5'-terminus comprising one or more non-natural nucleotides. Non-natural nucleotides include for example isocytosine (isoC) and isoguanine (isoG). The bridging oligonucleotide comprises a nucleotide sequence complementary to at least a portion of the second primer and a sequence identical to at least a portion of the first primer.

The first primer is annealed to the target nucleic acid and is extended with a polymerase enzyme to form a first duplex nucleic acid containing the target nucleic acid and a first nucleic acid. The target nucleic acid is separated and removed from the first nucleic acid.

The second primer is annealed to the first nucleic acid and extended with a polymerase enzyme to produce a second duplex nucleic acid containing the first nucleic acid and a second nucleic acid. The first nucleic acid is separated and removed from the second nucleic acid.

The bridging oligonucleotide anneals to both the 3'- and 5'-termini of the second nucleic acid bringing them together. The blunt ends are optionally ligated with ligase to produce a circular nucleic acid. The bridging oligonucleotide is extended in the presence of polymerase and non-natural nucleotide triphosphates complementary to the non-natural nucleotides of the second primer producing a concatemeric amplicon. The term "concatemeric" means that the amplicon contains multiple identical copies of the nucleic acid being extended; in this case a third nucleic acid.

The second primer is annealed to the third nucleic acid at one or more locations along the amplicon and extended by polymerase in the absence of the non-natural nucleotide triphosphates contained in the second primer to produce additional copies of the second nucleic acid.

The bridging oligonucleotide is annealed to the additional second nucleic acids to produce additional circular nucleic acids. The 3'- and 5'-termini of the additional circularized nucleic acids may be optionally joined by ligase. If the steps of annealing the second primer to the amplicon and annealing the bridging oligonucleotide to the additional second nucleic acids to produce additional circular nucleic acids are repeated, exponential amplification of the target nucleic acid is achieved.

A second aspect of the present invention is a method of amplifying a nucleic acid from a circularized stem-loop configuration nucleic acid template. The method utilizes first and second primers and a bridging oligonucleotide. The first primer has a sequence complementary to a first portion of the target nucleic acid and a 5'-tail sequence. The second primer has a sequence identical to a second portion of the target nucleic acid, a non-natural nucleotide cassette and a 5'-tail sequence that is the same as the 5'-tail sequence of the first primer. The bridging oligonucleotide has a nucleotide sequence that enables hybridization to sequences on both sides of the loop thereby straddling the base of the stem. The sequence includes a non-natural nucleotide residue complementary to the 3'-most non-natural nucleotide of the second primer.

The first primer is annealed to the target nucleic acid and extended with polymerase to produce a first duplex nucleic acid containing the target nucleic acid and a first nucleic acid. The target nucleic acid is separated and optionally removed from the first nucleic acid.

The second primer is annealed to the first nucleic acid and extended with polymerase to produce a second duplex nucleic acid containing the first nucleic acid and a second nucleic acid. The first nucleic acid is separated and optionally removed from the second nucleic acid.

The 3'- and 5'-terminal sequences of the second nucleic acid are complementary and hybridize to produce a stem-loop structure. The bridging oligonucleotide is annealed to a segment of the loop portion of the stem-loop structure bridging the gap between the hybridized 3'- and 5'-terminal sequences. The bridging oligonucleotide is extended by polymerase in the presence of non-natural nucleotide triphosphates complementary to the 3'-most non-natural nucleotide residue of the second primer to produce a concatemer amplicon containing multiple copies of a third nucleic acid.

A third primer comprising at its 5'-terminus the same non-natural nucleotide that is at the 3'-terminus of the tail segment of the second primer and a sequence that is the same as a portion of the 5'-non-tail terminus of second nucleic acid is annealed to one or more sites on the concatemer amplicon. The third primer is extended by polymerase in the absence of the non-natural nucleotide triphosphate of the same non-natural nucleotide in the third primer to produce a fourth nucleic acid. This fourth nucleic acid is hybridized to the bridging oligonucleotide to produce a circular template, which is optionally ligated, and the process is repeated, resulting in exponential amplification of the target nucleic acid.

Another aspect of the present invention is a method of amplifying a nucleic acid from a circularized target nucleic acid prepared utilizing an inverted primer. The method comprises a number of steps beginning with an inverted primer being mixed with a target nucleic acid. The inverted primer has a first sequence complementary to a first portion of the target nucleic acid on one end and an inverted nucleic acid sequence on the other end comprising a non-natural nucleotide cassette and a second sequence identical to a second portion of the target nucleic acid. The inverted primer is annealed to the target nucleic acid and extended with a polymerase enzyme to form a first duplex nucleic acid. The target nucleic acid is separated and removed from the first duplex nucleic acid to produce a first nucleic acid. The second sequence of the inverted primer binds to the first nucleic acid at a region complementary to the second portion of the target nucleic acid forming a circular nucleic acid. The primer is extended by a polymerase enzyme in the presence of non-natural nucleotides complementary to said non-natural nucleotides of the second primer to produce a concatemer amplicon. This amplicon contains multiple copies of the target nucleic acid. The amplicon is re-primed with the first primer and extended with polymerase in the absence of non-natural nucleotides complementary to non-natural nucleotides in the amplicon, producing multiple copies of a third nucleic acid. This process is repeated, resulting in exponential amplification of the target nucleic acid.

Other aspects of the invention are found throughout the specification.

DETAILED DESCRIPTION OF THE INVENTION

Figure 1A:
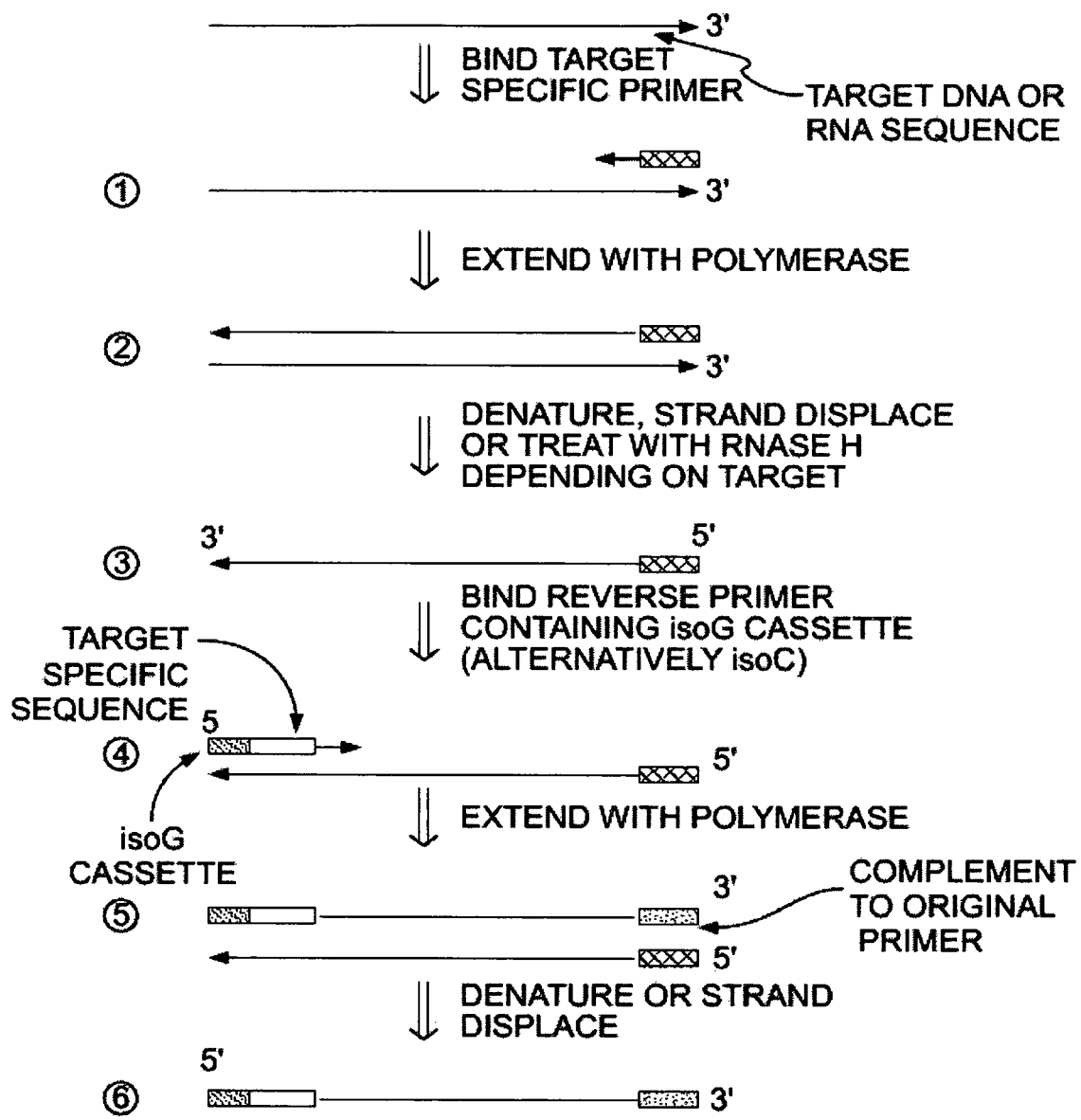
FIGS. 1A and B: is a schematic diagram of one aspect of the present invention wherein circularization occurs utilizing a bridging oligonucleotide.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "oligonucleotide" as used herein refers to a polymeric form of nucleotides, either ribonucleotides or deoxyribonucleotides, incorporating natural and non-natural nucleotides of a length ranging from at least 2, or generally about 5 to about 200, or more commonly to about 100. Thus, this term includes double- and single-stranded DNA and RNA. In addition, oligonucleotides may be nuclease resistant and include but are not limited to 2'-O-methyl ribonucleotides, phosphorothioate nucleotides, phosphorodithioate nucleotides, phosphoramidate nucleotides, and methylphosphonate nucleotides.

The term "target," "target sequence," or "target nucleic acid" as used herein refers to a nucleic acid that contains a polynucleotide sequence of interest, for which purification, isolation, capture, immobilization, amplification, identification, detection, quantitation, mass determination and/or sequencing, and the like is/are desired. The target sequence may be known or not known, in terms of its actual sequence.

The term "primer" or "primer sequence" as used herein are nucleic acids comprising sequences selected to be substantially complementary to each specific sequence to be amplified. More specifically, primers are sufficiently complementary to hybridize to their respective targets. Therefore, the primer sequence need not reflect the exact sequence of the target. Non-complementary bases or longer sequences can be interspersed into the primer, provided that the primer sequence has sufficient complementarity with the sequence of the target nucleic acid to permit hybridization and extension.

In addition, primers may be nuclease resistant and include primers that have been modified to prevent degradation by exonucleases. In some embodiments, the primers have been modified to protect against 3' or 5' exonuclease activity. Such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the primer(s) and/or probe(s) employed in an amplification reaction are protected against 3' and/or 5' exonuclease activity by one or more modifications.

The skilled artisan is capable of designing and preparing primers that are appropriate for extension of a target sequence. The length of primers for use in the methods and compositions provided herein depends on several factors including the nucleotide sequence identity and the temperature at which these nucleic acids are hybridized or used during in vitro nucleic acid extension. The considerations necessary to determine a preferred length for the primer of a particular sequence identity are well known to the person of ordinary skill.

The term "sample" as used herein refers to essentially any sample containing the desired target nucleic acid(s), including but not limited to tissue or fluid isolated from a human being or an animal, including but not limited to, for example, blood, plasma, serum, spinal fluid, lymph fluid, tears or saliva, urine, semen, stool, sputum, vomit, stomach aspirates, bronchial aspirates, organs, muscle, bone marrow, skin, tumors and/or cells obtained from any part of the organism; plant material, cells, fluid, etc.; an individual bacterium, groups of bacteria and cultures thereof; water; environmental samples, including but not limited to, for example, soil water and air; semi-purified or purified nucleic acids from the sources listed above, for example; nucleic acids that are the result of a process, such as template formation for sequencing, including next generation sequencing, sample processing, nuclease digestion, restriction enzyme digestion, replication, and the like.

The term "amplifying" or "amplification" as used herein refers to the process of creating nucleic acid strands that are identical or complementary to a complete target nucleic acid sequence, or a portion thereof, or a universal sequence that serves as a surrogate for the target nucleic acid sequence. The term "identical" as used herein refers to a nucleic acid having the same or substantially the same nucleotide sequence as another nucleic acid.

The term "nucleic acid" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions.

Nitrogenous bases may be conventional bases (A, G, C, T, U), non-natural nucleotides such as isoC and isoG, analogs thereof (e.g., inosine; The Biochemistry of the Nucleic Acids 5-36, Adams et al., ed., 11th ed., 1992), derivatives of purine or pyrimidine bases (e.g., $N^4$-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo [3,4-d]pyrimidine (e.g. U.S. Pat. Nos. 5,378,825, 6,949,367 and PCT No. WO 93/13121).

Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, Biochemistry 43(42):13233-41).

The term "releasing" or "released" as used herein refers to separating the desired amplified nucleic acid from its template, such as for example heating the duplex to a temperature that denatures the nucleic acid duplex forming two separate oligonucleotide strands.

The term "removing" as used herein refers to a variety of methods used to isolate one nucleic acid strand of a duplex from another, such as for example digestion of one of the strands of the duplex, enzymatic, thermal and/or chemical digestion, degradation and/or cleavage of one of the strands of the duplex, or denaturation/dissociation of the strands by heat, acoustic energy, chemicals, enzymes or a combination thereof or capturing one of the strands on a solid support and separating the strands chromatographically or electrophoretically.

The term "hybridization," "hybridize," "anneal" or "annealing" as used herein refers to the ability, under the appropriate conditions, for nucleic acids having substantial complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994). The term "substantial complementary" as used herein refers both to complete complementarity of binding nucleic acids, in some cases referred to as an identical sequence, as well as complementarity sufficient to achieve the desired binding of nucleic acids. Correspondingly, the term "complementary hybrids" encompasses substantially complementary hybrids.

The terms "tag region" or "tag sequence" refer to a user-defined nucleic acid sequence or sequences that are incorporated into an oligonucleotide or other nucleic acid structure, such as a primer, to provide one or more desired functionalities. Examples of such elements include, for example, adapters, sequencing primers, amplification primers, capture and/or anchor elements, hybridization sites, promoter elements, restriction endonuclease site, detection elements, mass tags, barcodes, binding elements, and/or non-natural nucleotides. Other elements include those that clearly differentiate and/or identify one or more nucleic acids or nucleic acid fragments in which a tag sequence has been incorporated from other nucleic acids or nucleic acid fragments in a mixture, elements that are unique in a mixture of nucleic acids so as to minimize cross reactivity and the like and elements to aid in the determination of sequence orientation. Some or all of the elements in a tag sequence can be incorporated into amplification products.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real time, single copy polymerase chain reaction in picoliter droplets," *Anal. Chem.* 79(22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics*, 4(1):41-47 (2004); all of which are incorporated by reference herein in their entirety.) In some embodiments, the amplification is by digital PCR.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proofreading capabilities. Enzymes that can be used with the methods include but are not limited to AmpliTaq, Phusion HS II, Deep Vent, and Kapa HiFi DNA polymerase.

The amplification product can be detected/analyzed using a number of methods known to those skilled in the art including, but not limited to, fluorescence, electrochemical detection, gel analysis and sequencing. Furthermore, the product can be quantitated using a number of methods known to those skilled in the art such as real time amplification. Quantitation can be normalized by comparison to so-called "house-keeping genes" such as actin or GAPDH or to an internal control that can be added to the reaction in a known amount. Such methods are well known and have been described in Sambrook and Russell, *Molecular Cloning: A Laboratory Manual* ($3_{rd}$ Ed.) (2001).

Instrumentation for performing the methods described herein is readily available. Such instruments can include instruments for real-time and end-point PCR assays, emulsion PCR, solid-phase PCR, melting curve analyses, and sequencing analyses. Such instruments include Life Technologies 7500 Fast Dx real-time instrument (which is also capable of high-resolution melting curve analyses) and the 3500xl capillary gel instruments. Other instruments known in the art to be useful in the methods of the present invention are also contemplated for use by one of skill in the art in practicing the methods of the present invention.

The present invention provides methods to perform target specific exponential rolling circle amplification comprising a variety of embodiments to re-prime amplicons that support multiple cycles of amplification. A variety of amplification techniques are known in the art. Patent application publication no.: 2011/0003305 A1 discloses some of these methods and is incorporate by reference herein in its entirety.

Figure 1B:
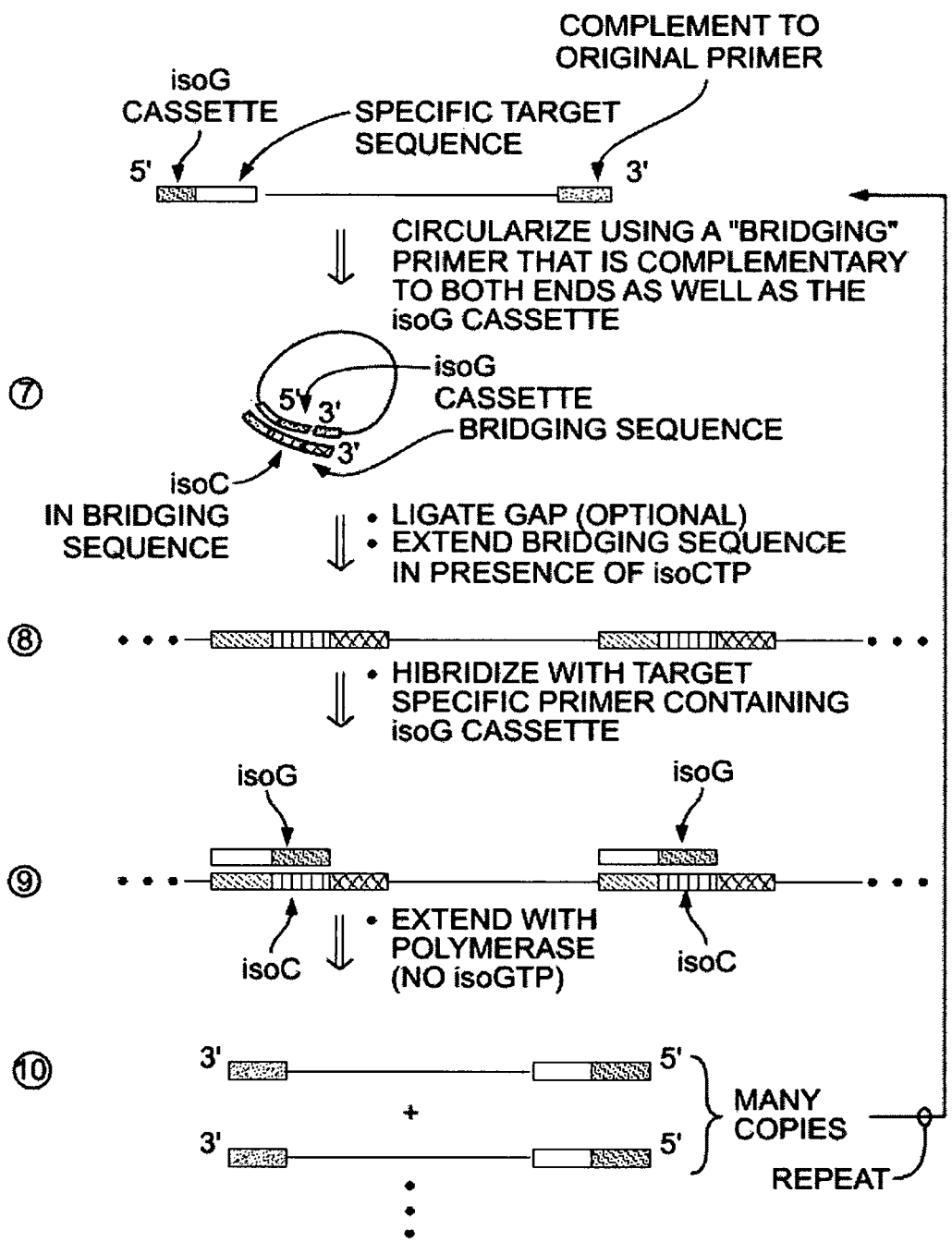

In one aspect of the present invention, a first primer comprising a complementary sequence to a specific target nucleic acid is hybridized to the desired target sequence and extended with polymerase, (e.g. a DNA polymerase or a reverse transcriptase) to produce a first duplex nucleic acid containing a first nucleic acid or in this example a first cDNA (FIG. 1). The target nucleic acid is separated from the first nucleic acid and optionally removed.

In one embodiment, this first cDNA is hybridized with a second primer comprising a sequence segment containing one or more non-natural nucleotides (e.g. isoG) at its 5'-terminus. The bound second primer is then extended by polymerase to produce a second duplex nucleic acid containing a second nucleic acid or in this example a second cDNA. The second cDNA is removed from the duplex and contacted with a bridging oligonucleotide comprising a sequence complementary to the second primer or a portion thereof and a sequence identical to the first primer or a portion thereof. The 3'- and 5'-termini of the second cDNA bind to their complementary sequences on the bridging oligonucleotide and the gap between the ends of the second cDNA is optionally closed using ligase (e.g. T4 DNA Ligase) resulting in the circularization of the second cDNA. The bridging oligonucleotide is then utilized as a primer and extended by polymerase using the circularized second cDNA as a template.

Deoxy-isocytosine triphosphate (isoC, which is the complement of isoG) is included in the extension reaction mixture to support polymerization across the isoG segment of the circularized second cDNA. The resulting amplicon is a long concatemer containing multiple copies of the second strand cDNA sequence, including an isocytosine cassette. The number of multiple copies of the second strand DNA sequence in the concatemeric amplicon can be as little as two up to several thousand.

Next, the second primer is hybridized to multiple sites along the amplicon and each of the primers is extended in the absence of isoG. Since no deoxy-isoG triphosphate is present in the reaction mixture, extension will terminate when the enzyme reaches an isoC cassette in the amplicon. This results in the production of multiple new copies of the second cDNA, which then can enter the reaction cycle again. This process continues, resulting in exponential amplification.

Figure 2:
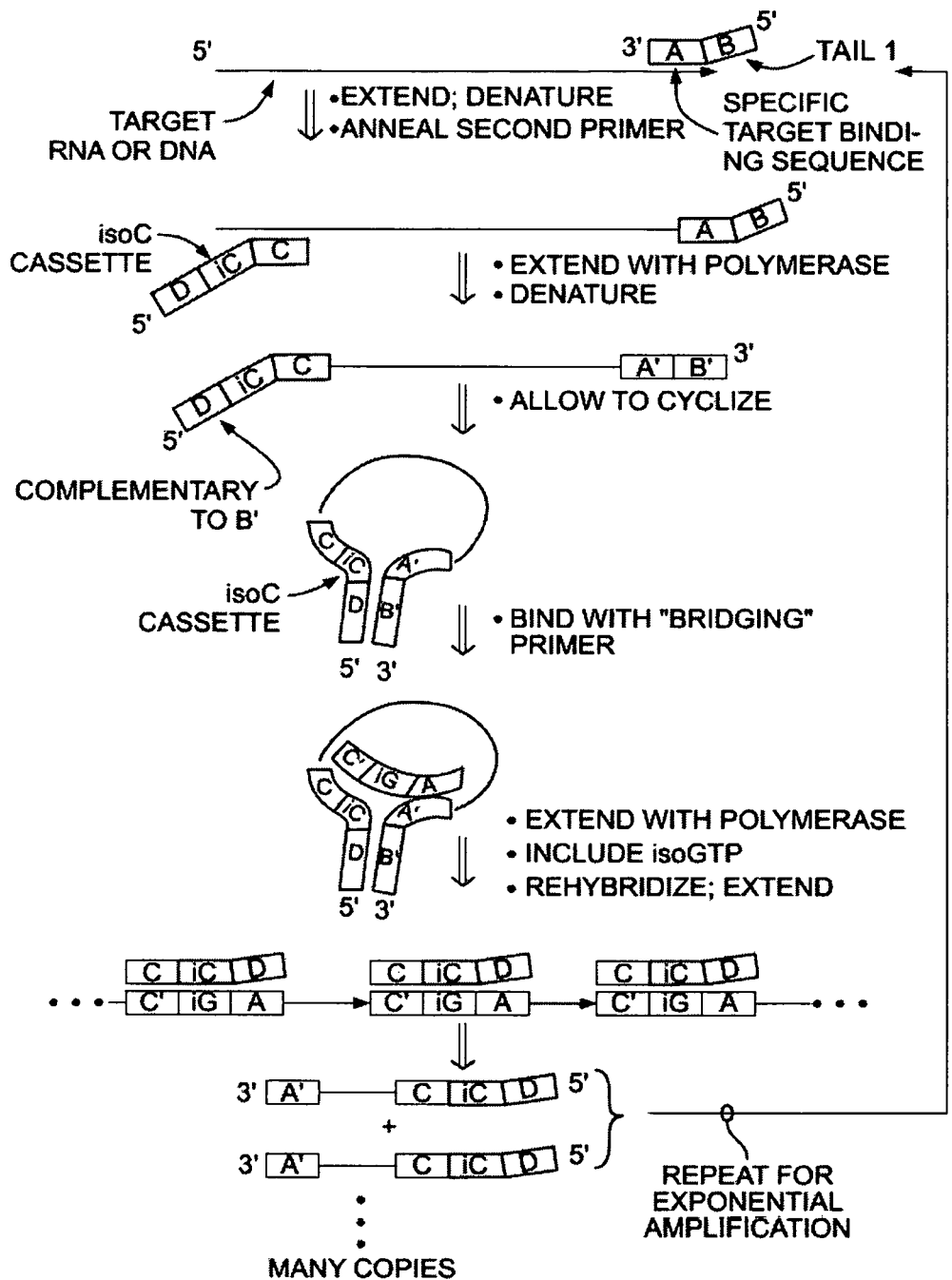
FIG. 2: is a schematic diagram of another aspect of the present invention wherein circularization occurs utilizing a complementary 5'-tail sequences introduced into the template during extension by the use of primers containing these sequences.

In a second embodiment, the first primer comprises a 5'-tag (or "tail") sequence and the second primer comprises a 5'-tag (or tail) sequence comprising a segment (or "cassette") (FIG. 2). At least a portion of the tag sequences are designed to be the same as each other. Consequently, following extension by the first and second primers to produce a second nucleic acid or in this example a second cDNA, the ends of this second cDNA form a stem-loop structure. A bridging oligonucleotide is designed to bind to two different segments of the loop such that it straddles the base of the stem-loop structure. The bridging oligonucleotide comprises an isoG residue that pairs with the isoC residue at the 3'-end of the 5'-stem.

The bridging oligonucleotide is utilized as a primer and extended by polymerase using the loop portion of the second cDNA as a template. Deoxy-isoG triphosphate is included in the extension reaction mixture to support polymerization across the isoC residue at the 3'-end of the 5'-stem. Furthermore, a polymerase is utilized that supports strand switching (e.g. Taq Polymerase I or Pfu DNA Polymerase) between the 2 segments of the loop portion that span the base of the stem structure. The resulting amplicon is a long concatemer containing multiple copies of the loop portion of the second cDNA sequence, including an isoG residue.

Next, a primer comprising an isoC residue at the 5' terminus and the sequence corresponding to the loop region complementary to the at least a portion of the 5'-portion of the bridge oligonucleotide is hybridized to multiple sites along the amplicon and each of the primers is extended by polymerase. Since no deoxy-IsoC triphosphate is present in the reaction mixture, extension will terminate when the enzyme reaches the next isoG residue in the amplicon. This results in the production of multiple new copies of the loop portion of the second cDNA, which then can enter the reaction cycle again, but now the bridging oligonucleotide is used to facilitate circularization of the template. The gap in the circle is optionally closed using a ligase. This process continues, resulting in exponential amplification.

Figure 3:
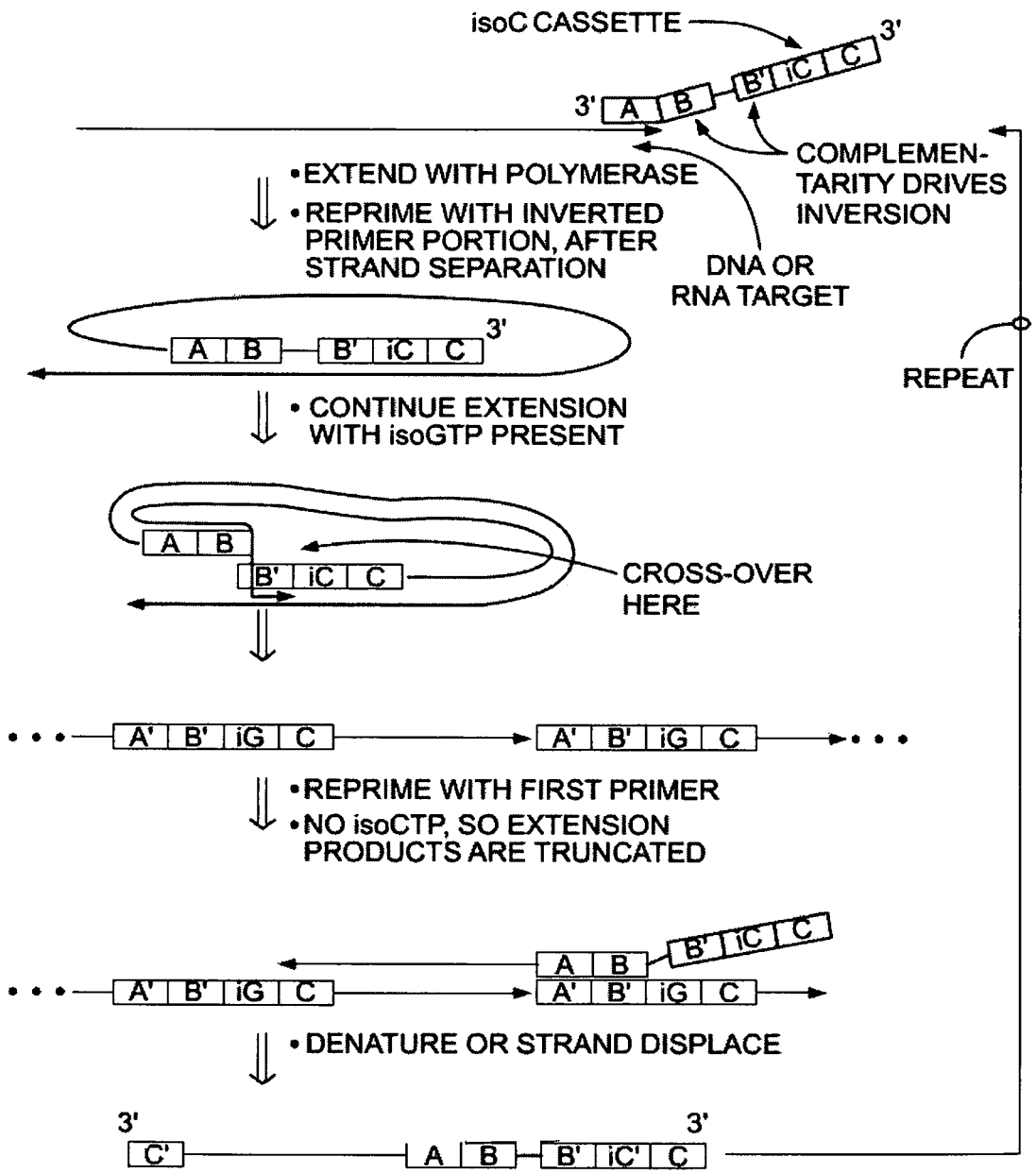
FIG. 3: is a schematic diagram of another aspect of the present invention wherein circularization occurs utilizing primers introduced into the template that promote circularization through strand cross-over during amplification.
Figure 4:
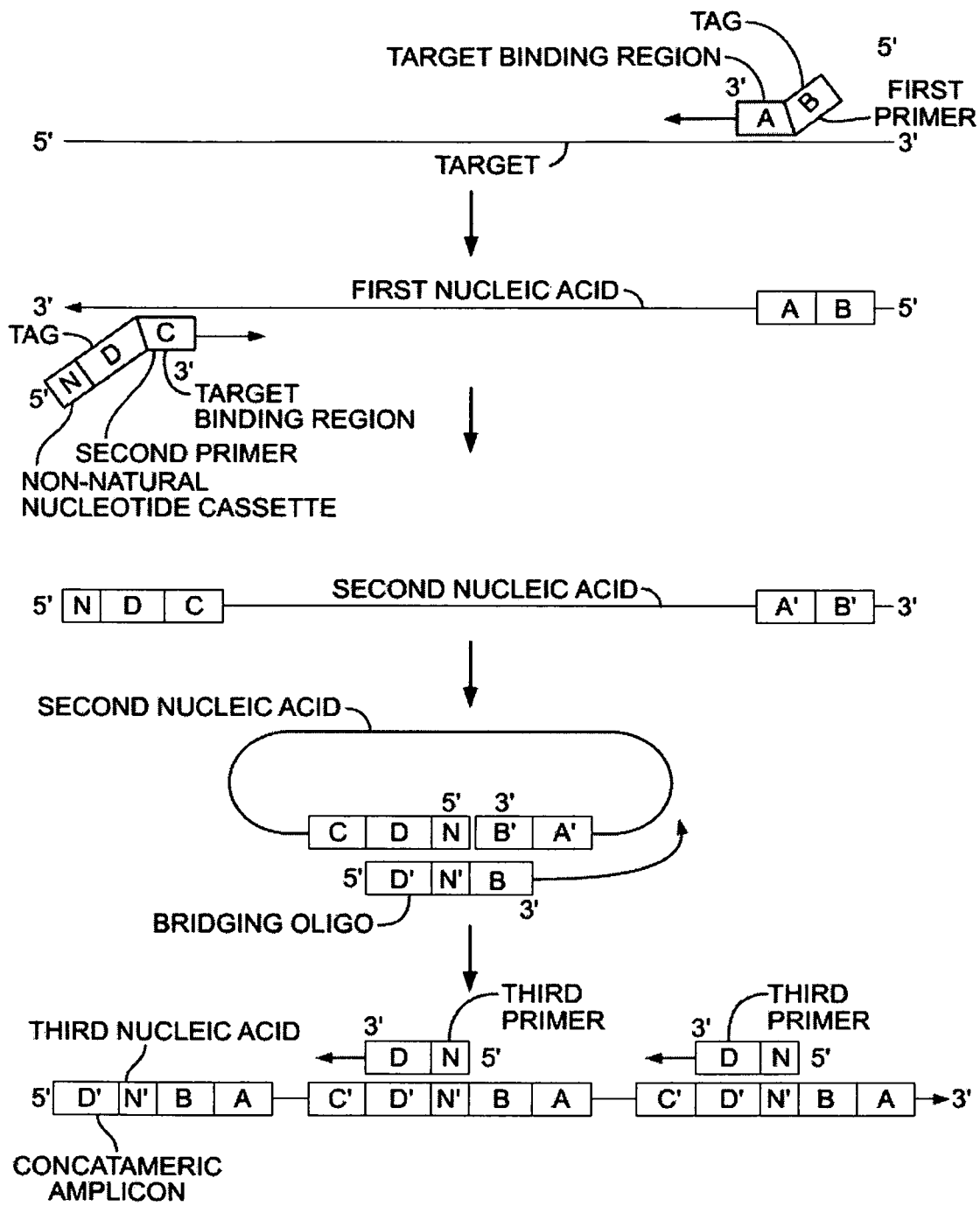
FIG. 4: is a schematic diagram of another aspect of the present invention showing target specific exponential rolling circle amplification.

In another aspect of the present invention, a unique primer is used that causes circularization and drives strand crossover during amplification (FIG. 3). The inverted primer has a first sequence on one end comprising a target binding region complementary to a first portion of the target nucleic acid and a tag region comprising one or more non-natural nucleotides (e.g., isoC) and a second sequence in reverse orientation on the other end comprising a target binding region identical to a second portion of the target nucleic acid. In a preferred mode, the first and second sequences are connected by an inverted linker. The target-binding region of the first sequence of the inverted primer is annealed to the target nucleic acid and extended with polymerase to form a first duplex nucleic acid. The target nucleic acid is removed from the first duplex nucleic acid to produce a first nucleic acid. The target-binding region of the second sequence of the inverted primer anneals to the first nucleic acid at a region complementary to the second portion of the target nucleic acid, forming a circular nucleic acid. The inverted primer is extended by polymerase in the presence of non-natural nucleotide triphosphates complementary to the non-natural nucleotides of the tag region of the first sequence of the inverted primer (e.g., isoG triphosphate). Each time the polymerase reaches the linker joining the two sequences of the inverted primer, the polymerase undergoes strand switching back to the first nucleic acid template, resulting in production of a concatemeric amplicon containing multiple copies of the target nucleic acid.

Next, a second primer, which is identical to the first sequence of the inverted primer, is hybridized to multiple sites along the amplicon and each of the primers is extended in the absence of isoC triphosphate. Since no isoC triphosphate is present in the reaction mixture, extension will terminate when the enzyme reaches an isoG in the amplicon. This results in the production of multiple copies of the complement of the target nucleic acid, which then can enter the reaction cycle again, but now the bridging oligonucleotide (as described in previous embodiments) is used to facilitate circularization of the template. The gap in the circle is optionally closed using a ligase. This cycle continues, resulting in exponential amplification of the target nucleic acid.

In another aspect of the present invention, the method utilizes a first, second and third primers and a bridging oligonucleotide. The first primer comprises a sequence "A" complementary to a first portion of the target nucleic acid and a tag sequence "B". The second primer comprises a sequence "C" identical to a second portion of the target nucleic acid, a tag sequence "D" and a cassette "N" at its 5'-end comprising one or more non-natural nucleotides (e.g. isoC and/or isoG). The bridging oligonucleotide comprises a nucleotide sequence "D'" complementary to at least a portion of the tag sequence "D" of the second primer, a nucleotide sequence "N'" complementary to the cassette "N" of the second primer and a nucleotide sequence "B" identical to at least a portion of the tag sequence "B" of the first primer.

The first primer is annealed to the target nucleic acid and extended by polymerase to form a first duplex nucleic acid containing the target nucleic acid and a first nucleic acid. The target nucleic acid is separated and removed from the first nucleic acid.

The second primer is annealed to the first nucleic acid and extended by polymerase to produce a second duplex nucleic acid containing the first nucleic acid and a second nucleic acid. The first nucleic acid is separated and removed from the second nucleic acid.

The bridging oligonucleotide anneals to both ends of the second nucleic acid, bringing them together. The blunt ends are optionally joined by ligase to produce a circular nucleic acid. The bridging oligonucleotide is extended by polymerase in the presence of non-natural nucleotide triphosphates complementary to the non-natural nucleotides of cassette "N" the second primer to produce a concatemeric amplicon.

The third primer is annealed to the third nucleic acid at one or more locations along the amplicon and extended by polymerase in the absence of the non-natural nucleotide triphosphate contained in cassette "N" of the second primer to produce additional copies of the second nucleic acid.

The bridging oligonucleotide is annealed to the additional second nucleic acids and the process is repeated to achieve exponential amplification of the target nucleic acid.

Figure 5A:
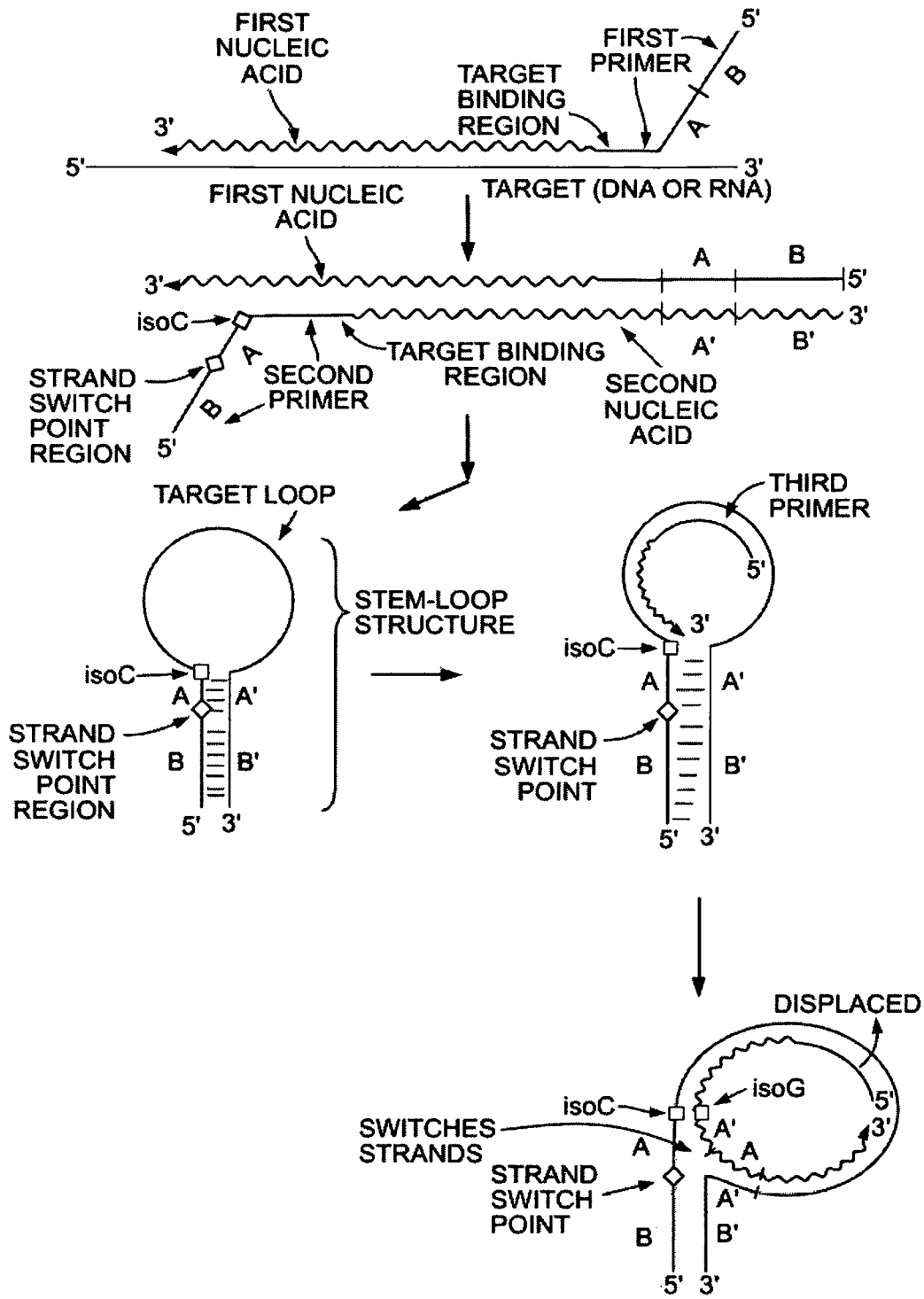
FIGS. 5A and B: is a schematic diagram of another aspect of the current invention wherein circularization occurs via a strand switching process in a stem loop nucleic acid structure.

In another aspect of the present invention, the method utilizes a first primer comprising a target binding region and a 5'-tag sequence comprising 2 regions A and B, and the second primer comprising a target binding region and a 5'-tag sequence comprising an isoC segment, region A, a strand switch point region and a region B (FIG. 5A). The isoC region contains at least one isoC nucleotide, although other non-natural nucleotides may be utilized. The strand switch point region contains a component or components that halt the progress of a polymerase on that strand and thereby assist the polymerase to switch to another strand at that point. Examples of such components include but are not limited to a non-nucleotide linker arm (e.g., C3 spacer, Glenn Research, Sterling, Va.) and a modified nucleotide (such as 2'-O-Methyl nucleotide, TriLink BioTechnologies, San Diego, Calif.).

The first primer is annealed to the target nucleic acid and extended with polymerase to produce a first duplex nucleic acid containing the target nucleic acid and a first nucleic acid. The target strand is removed from the first nucleic acid, and the second primer is annealed to the first nucleic acid. The second primer is extended with polymerase to produce a second duplex containing the first nucleic acid and a second nucleic acid. The first nucleic acid is removed from the second nucleic acid and the second nucleic acid forms a stem-loop structure (FIG. 5A).

A third primer that is complementary to a region of the loop of the stem-loop structure is annealed to the loop. The third primer is extended by polymerase. Deoxy-isoG triphosphate is included in the extension reaction mixture to support polymerization across the isoC residue(s) at the 3'-end of the 5'-stem. The polymerase begins to read down the arm of the 5'-stem, unwinding the stem as it proceeds and thus rendering the A' segment of the stem single stranded. The polymerase stops reading down the arm of the 5'-stem when it reaches the strand switch point region, and then switches to the single stranded A' region from the 3'-stem. Extension continues around this same path many times, incorporating an isoG residue(s) across from the isoC region each time around. This results in a long concatemer amplicon containing multiple copies of a segment containing isoG (one or more residues), the complement to the target loop portion of the second cDNA sequence and the A and A' regions.

A fourth primer comprising one or more isoC residues on the 5'-terminus and a portion of the target loop sequence that binds to the region of the amplicon immediately to the 5'-side of the isoG residue(s) (FIG. 5B) is annealed to the amplicon at multiple locations and extended by polymerase. Since there is no deoxy-isoC triphosphate in the polymerization mix, extension terminates when the polymerase reaches the isoG regions of the amplicon, thus creating multiple copies of a third nucleic acid containing, from the 5' to 3', one or more isoC residues the target loop sequence; and the A' and A regions. These multiple copies of the third nucleic acid can then enter the cycle again, starting at the point where the first nucleic acid is annealed to the target nucleic acid (a copy of which is contained in each third nucleic acid), thus amplifying the target nucleic acid exponentially.

Figure 5B:
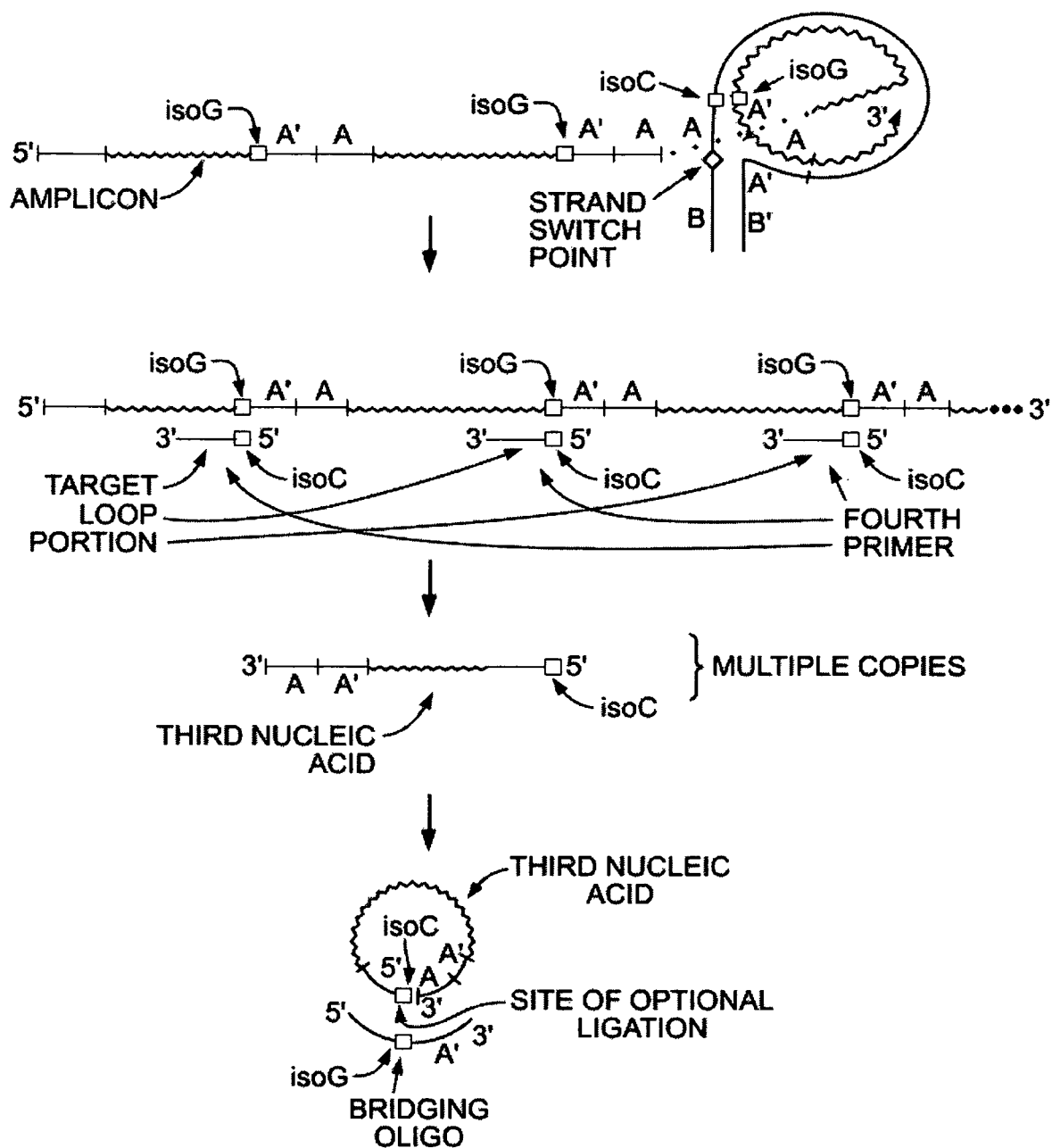

Alternatively, a bridging oligonucleotide complementary to a portion of both the 5' and 3' ends of the third nucleic acid can be used to create a circular template, which is optional ligated (FIG. 5B). The bridging oligonucleotide is extended by polymerase, again creating a long concatemeric amplicon, thus exponentially amplifying the target nucleic acid.

In other embodiments of this aspect, only one of the first or second primers is equipped with a tag. The tag sequences may also contain other functional segments, including but not limited to, for example, an adapter(s), a sequencing primer(s), a tag primer(s), a barcode, a capture site(s) and/or a detection site(s). In addition, one or more of the primers may be bound to a solid support(s).

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference. For example, many of the wash steps cited in the different methods are optional as are some of the steps that remove and/or separate two nucleic acid strands from one another. Not performing at least some of the wash and/or separation steps will afford a faster, simpler and more economical work flow, while still achieving the desired results. In another example, the stepwise addition/binding of certain oligonucleotides and/or target nucleic acids in the exemplified methods may be combined. Furthermore, a variety of polymerases, extension conditions and other amplification protocols known to those skilled in the art may be used in various steps or combination of steps in the methods described above. Other obvious modifications to the methods disclosed that would be obvious to those skilled in the art are also encompassed by this invention.

What is claimed is:

1. A method of amplifying a nucleic acid from a circularized target nucleic acid, said method comprising the steps of:

A. annealing a first primer to a target nucleic acid in a mixture comprising said first primer and said target nucleic acid wherein said first primer has a sequence complementary to a first portion of said target nucleic acid and a 5'-tail sequence and extending said first primer with polymerase to form a first duplex nucleic acid;

B. optionally removing said target nucleic acid from said first duplex nucleic acid to produce a first nucleic acid;

C. annealing a second primer to said first nucleic acid, wherein said second primer has a sequence substantially identical to a second portion of said target nucleic acid, a non-natural nucleotide cassette and a 5'-tail sequence that is substantially identical to said 5'-tail sequence of said first primer, and extending said second primer with polymerase to produce a second duplex nucleic acid, and optionally removing said first nucleic acid from said second duplex nucleic acid to produce a second nucleic acid wherein the ends of said second nucleic acid hybridize forming a stem-loop structure;

D. annealing a bridging oligonucleotide to said stem-loop structure, wherein said bridging oligonucleotide has a nucleotide sequence that enables hybridization to sequences on both sides of the loop, thereby straddling the base of the stem-loop structure, and wherein the bridging oligonucleotide includes a non-natural nucleotide residue complementary to the 3'-most non-natural nucleotide of the second primer, and adding non-natural nucleotide triphosphate that is complementary to the 3'-most non-natural nucleotide residue of said second primer and extending said bridging oligonucleotide with polymerase to produce a concatemer amplicon containing multiple copies of a third nucleic acid;

E. annealing a third primer to said concatemer amplicon at one or more sites wherein said third primer comprises at its 5'-terminus the same non-natural nucleotide that is at the 3'-terminus of the tail segment of the second primer and a sequence that is substantially identical to a portion of the 5'-non-tail terminus of the second nucleic acid, and extending said third primer by polymerase to produce multiple copies of a fourth nucleic acid and optionally removing said fourth nucleic acid from said concatemer amplicon, wherein repeating the steps D and E results in exponential amplification of said target nucleic acid.

2. A method according to claim 1, further comprising the step of ligating said stem loop structure following annealing of said bridging oligonucleotide.

3. A method of amplifying a nucleic acid from a circularized target nucleic acid, said method comprising the steps of:

A. annealing an inverted primer to a target nucleic acid in a mixture comprising said inverted primer and a target nucleic acid wherein said inverted primer has a sequence complementary to a first portion of said target nucleic acid on one end and an inverted sequence comprising a non-natural nucleotide cassette and a nucleotide sequence identical to a second portion of said target nucleic acid on the other end, extending said inverted primer with polymerase to form a first duplex nucleic acid and optionally removing said target nucleic acid from said first duplex nucleic acid to produce a first nucleic acid wherein said inverted sequence of said inverted primer hybridizes the complementary sequence of said second portion of said target nucleic acid forming a circular nucleic acid; and B. adding non-natural nucleotide triphosphates that are complementary to said non-natural nucleotides of said inverted primer, and extending said inverted primer with polymerase to produce a concatemeric amplicon containing multiple copies of said target nucleic acid, wherein repeating said adding and extending steps exponentially amplifies said target nucleic acid.

\* \* \* \* \*